United States Patent
Kimura

(10) Patent No.: US 7,202,293 B2
(45) Date of Patent: *Apr. 10, 2007

(54) ANTIMICROBIAL RESIN COMPOSITION

(75) Inventor: Yoshikazu Kimura, Osaka (JP)

(73) Assignee: Fuji Chemical Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/349,807

(22) Filed: Feb. 8, 2006

(65) Prior Publication Data

US 2006/0141056 A1    Jun. 29, 2006

Related U.S. Application Data

(63) Continuation of application No. 10/350,278, filed on Jan. 23, 2003, now Pat. No. 7,041,723.

(51) Int. Cl.
*C08K 3/10* (2006.01)

(52) U.S. Cl. ................. 524/413; 524/415; 524/434; 524/450

(58) Field of Classification Search .............. 524/413, 524/415, 434, 450
See application file for complete search history.

(56) References Cited

U.S. PATENT DOCUMENTS

| | | | |
|---|---|---|---|
| 4,911,898 A | 3/1990 | Hagiwara et al. | |
| 4,911,899 A | 3/1990 | Hagiwara et al. | |
| 5,556,618 A | 9/1996 | Ando et al. | |
| 6,187,456 B1 | 2/2001 | Lever | |

FOREIGN PATENT DOCUMENTS

| | | |
|---|---|---|
| JP | 63-28402 B2 | 6/1988 |
| JP | 3-124810 A | 10/1989 |
| JP | 6-10126 B2 | 4/1991 |
| JP | 3-153745 A | 7/1991 |
| JP | 3-181538 A | 8/1991 |
| JP | 5-190389 B1 | 12/1993 |
| JP | 8-302174 A | 11/1996 |

*Primary Examiner*—Peter D. Mulcahy
(74) *Attorney, Agent, or Firm*—The Webb Law Firm

(57) ABSTRACT

A resin composition having excellent dispersibility, discoloration resistance and antimicrobial properties by blending a resin (A) with an antimicrobial agent (B) in which at least one kind of metal ion selected from the group consisting of silver, copper, zinc and tin is supported on zeolite, and an antimicrobial agent (C) that includes a silver ion-containing phosphate as an active ingredient, or an antimicrobial agent (D) made of a soluble glass powder containing silver ion.

7 Claims, No Drawings

ANTIMICROBIAL RESIN COMPOSITION

CROSS-REFERENCE TO RELATED APPLICATION

This application is a continuation of U.S. patent application Ser. No. 10/350,278 filed Jan. 23, 2003, now U.S. Pat. No. 7,041,723, which is incorporated herein by reference in its entirety.

BACKGROUND OF THE INVENTION

The present invention relates to antimicrobial resin compositions. More specifically, the present invention relates to antimicrobial resin compositions having excellent antimicrobial properties and excellent dispersibility and discoloration resistance.

With recent increasing consciousness of cleanliness of consumers and consumer needs in the pursuance of high-value-added products, it has been promoted to subject products to antimicrobial processing in various fields, for example, stationery such as ball-point pens and erasers, miscellaneous goods of daily use including kitchenware such as cutting boards and bathroom ware such as bathtubs, home electric appliances such as telephone sets, rice cookers, and refrigerators, building materials such as floor materials and wall materials, and textile products such as bed sheets, pajamas, sanitary clothing, and curtains.

There are generally two kinds of methods for subjecting products to antimicrobial processing. In one method, an antimicrobial agent is added to resin and kneaded in the stage of manufacturing products such as plastic molded articles, synthetic textiles and films. The antimicrobial properties of the antimicrobial-processed products obtained by this method last for a long time. In another method, these products are coated with a coating agent containing an antimicrobial agent. The antimicrobial-processed products obtained by this method tend to lose their antimicrobial properties gradually because the coated layer is peeled off through use. Either method is appropriately selected depending on the materials of the commercial products, the manufacturing conditions of the commercial products, the required characteristics, and the types of antimicrobial agents to be used.

On the one hand, antimicrobial agents are classified broadly into organic antimicrobial agents and inorganic antimicrobial agents. Organic antimicrobial agents raise health concerns and many of them do not have sufficient antimicrobial activity. On the other hand, inorganic antimicrobial agents employ metal ions, typically, silver ion, and are excellent in safety and antimicrobial activity. Accordingly, in general, for the above-described products, inorganic antimicrobial agents are used.

The antimicrobial activity of inorganic antimicrobial agents employing metal ions depends on the dissolution rate of the metal ions that are used. When inorganic antimicrobial agents employing metal ions are blended into resin, the metal ions react with additives such as catalyst residue, antioxidant, photostabilizer or the like in the resin and therefore degrade the antimicrobial activity. Moreover, the resin is discolored by light or heat.

In the case of resins molded by methods such as injection molding, extrusion molding or blow molding, antimicrobial agents are generally added to the resin in the stage of masterbatch molding, and it is necessary that antimicrobial agents are dispersed effectively into the resin and on the surface of the resin in order to maximize the antimicrobial ability.

There is a demand for a resin composition that does not change its color to yellowish-brown through light or heat and has excellent dispersibility in a resin and further provides significant antimicrobial properties.

SUMMARY OF THE INVENTION

In order to solve the above problems, the inventors of the present invention conducted research and found that by combining specific antimicrobial agents, drawbacks of each antimicrobial agent are complemented and each function is exhibited synergistically and the above problems can be solved, thus achieving the present invention.

The present invention relates to an antimicrobial resin composition, wherein a resin (A) is blended with an antimicrobial agent (B) in which at least one kind of metal ion selected from the group consisting of silver, copper, zinc and tin is supported on zeolite, and an antimicrobial agent (C) that includes a silver ion-containing phosphate as an active ingredient, or a soluble glass powder (D) containing silver ion.

In a preferable embodiment, 0.01 to 10 parts by weight of the antimicrobial agent (B) and 0.01 to 10 parts by weight of the antimicrobial agent (C) are blended with respect to 100 parts by weight of the resin (A).

In another preferable embodiment, 0.01 to 10 parts by weight of the antimicrobial agent (B) and 0.01 to 10 parts by weight of the antimicrobial agent (D) are blended with respect to 100 parts by weight of the resin (A).

In a preferable embodiment, the resin (A) is a thermoplastic resin. In a further preferable embodiment, this thermoplastic resin is polyolefin.

DETAILED DESCRIPTION OF THE INVENTION

There is no particular limitation regarding the resin (A) used in the present invention. Examples of the resin (A) include a thermoplastic resin, a thermosetting resin, and a reproduced or semi-synthetic polymer. Examples of thermoplastic resins include polyolefin, polystyrene, polyamide, polyester, polyvinyl alchohol, polycarbonate, polyacetal, ABS resin, acrylic resin, fluorocarbon resin, polyurethane elastomer, and polyester elastomer. Examples of thermosetting resins include phenolic resin, urea resin, melamine resin, unsaturated polyester resin, epoxy resin, and urethane resin. Examples of the regenerated or semi-synthetic polymer include rayon, cupra, acetate, and triacetate.

In particular, polyolefins contain a chlorine-compound (titanium tetrachloride, titanium trichloride, etc.) derived from a Ziegler Natta catalyst and additives containing chlorine (chlorinated paraffin, perchlor penta cyclodecane, and the like) such as flame retardant, and therefore polyolefins are easily discolored by blending an antimicrobial agent. However, when the antimicrobial agent (B) and the antimicrobial agent (C) or (D) used in the present invention are blended with a polyolefin, discoloration is significantly inhibited and antimicrobial properties are improved. Accordingly, polyolefin is preferable as a resin used in the present invention because of the remarkable effects as described above.

There is no particular limitation regarding the polyolefin. Examples of polyolefins include a homopolymer of α-olefin such as ethylene, propylene, butane-1, hexane-1, and 4-methyl pentene-1; a copolymer of ethylene and propylene or other α-olefins; or at least two kinds of copolymer of these α-olefins. Among these examples, polyethylene (for example, low density polyethylene, linear low density polyethylene, medium density polyethylene, high density polyethylene, or the like) and polypropylene are preferable. The polypropylene is not limited to homopolymer. A random copolymer or a block copolymer of propylene and other α-olefins containing 50 mol % or more, preferably 80 mol % or more of propylene components may also be used. Examples of comonomers that can be copolymerized with propylene include ethylene and other α-olefins, and ethylene is particularly preferable.

In the antimicrobial agent (B) used in the present invention, at least one kind of metal ion selected from the group consisting of silver, copper, zinc, and tin is supported on zeolite. This antimicrobial agent (B) is characterized in that its safety has been confirmed by the test regarding toxicity and impact on environment under the US EPA guideline, and that the antimicrobial agent (B) is based on zeolite, and that it has a low hardness of 2 to 3 and contains crystal water. Due to the characteristic of containing crystal water, the antimicrobial agent (B) has the advantage that it suppresses heat from being generated during kneading of the resin. On the other hand, it has the drawback that depolymerization occurs when it is kneaded into polyester.

However, this drawback of the antimicrobial agent (B) is resolved by mixing with an antimicrobial agent (C) or an antimicrobial agent (D), which will be described later, improving the antimicrobial activity.

Examples of the antimicrobial agent (B) used in the present invention include the antimicrobial agents described in Japanese Patent Publication (Tokko) No. 63-28402. The average particle diameter of the antimicrobial agent (B) is preferably 0.2 to 10 μm, and more preferably 2 to 5 μm. If the particle diameter is less than 0.2 μm or more than 10 μm, the dispersibility of the antimicrobial agent (C) or the antimicrobial agent (D) is not improved. As a commercially available product, for example, there is "BACTEKILLER (product name) manufactured by Kanebo LTD."

The antimicrobial agent (C) used in the present invention is an antimicrobial agent that includes a silver ion-containing phosphate as its active ingredient. An example of the antimicrobial agent (C) is described in Japanese Patent Publication (Tokko) No. 6-10126. A preferable antimicrobial agent (C) includes a compound expressed by the following general formula as its active ingredient:

$$Ag_xH_yA_zM_2(PO_4)_3$$

where A is an alkali metal, M is Zr, Ti or Sn, x, y, and z are positive numbers smaller than 1, and x+y+z=1.

The antimicrobial agent (C) has the advantages that it causes discoloration of the resin to a smaller degree than the antimicrobial agent (B), and that it does not contain crystal water. However, the antimicrobial agent (C) has the drawbacks that the zirconium or titanium compound contained as a metal has a high hardness, the antimicrobial agent (C) tends to bring dirt of a manufacturing machine into the resin in the stage of kneading, and the antimicrobial activity is somewhat low.

However, these drawbacks of the antimicrobial agent (C) are resolved by mixing with the above-mentioned antimicrobial agent (B). The average particle diameter of the antimicrobial agent (C) is preferably 0.3 to 5 μm, and more preferably 0.5 to 2 μm. If the particular diameter is less than 0.3 μm, the dispersion tends to be poor when the antimicrobial agent (C) is added to the resin. If the particle diameter is more than 5 μm, the mechanical properties of a molded article are lowered.

The antimicrobial agent (D) used in the present invention is made of a soluble glass powder containing silver ion. An example of the antimicrobial agent (D) is described in Japanese Laid-Open Patent Publication (Tokkai) No. 3-124810. The antimicrobial agent (D) advantageously prevents the resin from being discolored and does not contain crystal water, and has a high degree of freedom in the composition ratio. On the other hand, the antimicrobial agent (D) has the following drawbacks: The particle shape is non-uniform and the hardness is high, so that the dispersibility is poor and dirt of manufacturing machine is easily brought into the resin in the stage of kneading. However, these drawbacks of the antimicrobial agent (D) are resolved by mixing it with the above-mentioned antimicrobial agent (B). The average particle diameter of the antimicrobial agent (D) is preferably 0.3 to 10 μm, and more preferably 0.5 to 2 μm. If the particle diameter is less than 0.3 μm, the dispersion tends to be poor when the antimicrobial agent (C) is added to the resin. If the particle diameter is over 10 μm, the mechanical physical properties of the molded article are lowered.

When the antimicrobial resin composition of the present invention comprises the resin (A) and the antimicrobial agents (B) and (C), it is preferable that 0.01 to 10 parts by weight of the antimicrobial agent (B) and 0.01 to 10 parts by weight of the antimicrobial agent (C) are blended with respect to 100 parts by weight of the resin (A). Preferably, 0.01 to 1 parts by weight of the antimicrobial agent (B) and 0.1 to 5 parts by weight of the antimicrobial agent (C) are blended. If the antimicrobial agent (B) is less than 0.01 parts by weight, the dispersibility is hardly improved. On the other hand, if the antimicrobial agent (B) is more than 10 parts by weight, the resin is easily discolored. If the antimicrobial agent (C) is less than 0.01 parts by weight, the antimicrobial properties cannot be exhibited. On the other hand, if the antimicrobial agent (C) is more than 10 parts by weight, the dispersion tends to be poor, dirt is brought in when the agent is added to the resin and kneaded, and the resin is discolored by heat.

When the antimicrobial resin composition of the present invention consists of the resin (A) and the antimicrobial agents (B) and (D), it is preferable that 0.01 to 10 parts by weight of antimicrobial agent (B) and 0.01 to 10 parts by weight of antimicrobial agent (D) are blended with respect to 100 parts by weight of the resin (A). Preferably, 0.01 to 1 parts by weight of antimicrobial agent (B) and 0.01 to 5 parts by weight of antimicrobial agent (D) are blended. If the antimicrobial agent (B) is less than 0.01 parts by weight, the dispersibility is hardly improved. On the other hand, if the antimicrobial agent (B) is more than 10 parts by weight, the resin is easily discolored. If the antimicrobial agent (D) is less than 0.01 parts by weight, the antimicrobial properties cannot be exhibited. On the other hand, if the antimicrobial agent (D) is more than 10 parts by weight, the dispersion tends to be poor, dirt is brought in when the agent is added to the resin and kneaded, and the resin is discolored by heat.

In order to further improve the thermostability and the heat moldability, an antioxidant, an inorganic filler (such as talc, mica, and wallastonite), a heat stabilizer, a photostabilizer, a flame retardant, a plasticizer, an antistat, a releasing agent, a foaming agent, a nucleating agent may be added to the antimicrobial resin composition of the present invention.

The antimicrobial resin composition of the present invention can be obtained in the following manner, for example, when the resin (A) is a thermoplastic resin: the resin (A), the antimicrobial agent (B), the antimicrobial agent (C) or antimicrobial agent (D), and if necessary, additives such as an antioxidant are blended, premixed, and then kneaded by an extruder.

EXAMPLES

Hereinafter, the present invention will be described in detail by way of examples and comparative examples. However, the present invention is not limited to these examples.

Examples 1 to 8

With respect to 100 parts by weight of a polypropylene resin as the resin (A), four kinds of zeolite of antimicrobial agent "Bactekiller (manufactured by Kanebo LTD.)" that have the silver ion contents (wt %) and average particle sizes shown in table 1 were used as the antimicrobial agent (B), an antimicrobial agent of a zirconium phosphate was used as the antimicrobial agent (C), and a glass-based antimicrobial agent was used as the antimicrobial agent (D). The antimicrobial agent (B) and the antimicrobial agent (C) or the antimicrobial agent (D) were blended in the ratio shown in the table 1, and preliminary kneading was performed with a Henschel Mixer. The obtained mixture was melt-kneaded with an extruder (50 mm φ, single screw) and then pelletized. The temperature of the resin in the extruder was 190° C. at the rear section of the cylinder, 200° C. at the middle section of the cylinder, 220° C. at the front section of the cylinder, and 220° C. at the dies section.

The dispersibility, the discoloration properties, and the antimicrobial properties of the obtained antimicrobial resin composition (pellets) are measured and evaluated by the following method. The table 1 shows the results.

(1) Dispersibility: The resin to which the antimicrobial agent had been added was subjected to melt-pressing at 250° C. to produce a thin film sample. Then, the size of coarse particles of the thin film sample was measured by a transmission optical microscope and evaluated as follows.

favorable: 0 coarse particle with 20 μm or more/mm$^2$
normal: 1 to 5 coarse particles with 20 μm or more/mm$^2$
defective: 6 or more coarse particles with 20 μm or more/mm$^2$ (2) Discoloration resistance: A test of discoloration resistance was conducted for 25 hours with a testing apparatus for light resistance promotion (Xenon Weather Meter), and then a color difference ΔE was measured with a color-difference meter. The larger the value of ΔE is, the higher the degree of discoloration is.

favorable: ΔE of 0.1 or more and less than 0.6
normal: ΔE of 0.6 or more and less than 1.1
defective: ΔE of 1.1 or more (3) Antimicrobial properties: The antimicrobial properties were evaluated based on the method defined in a Test for Antimicrobial Activity for antimicrobial products (Society of Industrial-Technology for Antimicrobial Articles).
Test method: Film Adherence Method
Evaluated bacteria:
    *Escherichia coli* and *Staphylococcus aureus*
Contact time of bacteria and test sample: 24 hours
Evaluation: bacteria were contacted with a resin molded article to which the antimicrobial agent was added, and was covered with the film. Then, 24 hours later, the number of bacteria was counted.
favorable: A decreasing rate from the number of inoculated bacteria of 1/100 or more
normal: A decreasing rate from the number of inoculated bacteria of 1/10 or more and less than 1/100.
defective: A decreasing rate from the number of inoculated fbacteria of less than 1/10.

Comparative Examples 1 to 7

The antimicrobial resin compositions were obtained by the same procedures as in the Examples 1 to 8 except that the resin (A), and the antimicrobial agents (B), (C), and (D) were blended in the ratio shown in Table 1. Then, their physical properties were measured and evaluated in the same manner as in the Examples 1 to 8. Table 1 shows the results.

TABLE 1

| | | | Comparative Examples | | | | | | |
|---|---|---|---|---|---|---|---|---|---|
| | | | 1 | 2 | 3 | 4 | 5 | 6 | 7 |
| Composition | A | PP resin | 100 | 100 | 100 | 100 | 100 | 100 | 100 |
| | B* | (Ag: 0.1) 2 μm | | 1.0 | | | | | |
| | | (Ag: 0.1) 5 μm | | | 1.0 | | | | |
| | | (Ag: 2.0) 2 μm | | | | 1.0 | | | |
| | | (Ag: 2.0) 5 μm | | | | | 1.0 | | |
| | C | Zirconium-phosphate | | | | | | 1.0 | |
| | D | Glass | | | | | | | 1.0 |
| Properties | | Dispersibility | G | G | G | G | G | U | B |
| | | Color fastness | G | U | G | B | U | G | U |
| | | Antimicrobial properties | B | U | U | G | G | U | G |

| | | | Examples | | | | | | | |
|---|---|---|---|---|---|---|---|---|---|---|
| | | | 1 | 2 | 3 | 4 | 5 | 6 | 7 | 8 |
| Composition | A | PP resin | 100 | 100 | 100 | 100 | 100 | 100 | 100 | 100 |
| | B* | (Ag: 0.1) 2 μm | 0.5 | | | | | 0.5 | | |
| | | (Ag: 0.1) 5 μm | | 0.5 | | | | | 0.5 | |
| | | (Ag: 2.0) 2 μm | | | 0.5 | | | | | 0.5 |
| | | (Ag: 2.0) 5 μm | | | | 0.5 | | | | 0.5 |
| | C | Zirconium | 0.5 | 0.5 | 0.5 | 0.5 | | | | |

TABLE 1-continued

| | | | | | | | | | | | |
|---|---|---|---|---|---|---|---|---|---|---|---|
| | D | phosphate Glass | | | | | | 0.5 | 0.5 | 0.5 | 0.5 |
| Properties | | Dispersibility | G | G | G | G | G | G | G | G |
| | | Color fastness | G | G | G | G | G | G | G | G |
| | | Antimicrobial properties | G | G | G | G | G | G | G | G |

B*: zeolite
G: favorable
U: normal
B: defective
The above numbers indicate parts by weight.

As seen from the comparison between Examples 1 to 8 and Comparative Examples 1 to 7 in Table 1, by using the antimicrobial agents (B) and (C) together or using the antimicrobial agents (B) and (D) together, resin compositions having better dispersibility, higher discoloration resistance and more excellent antimicrobial properties are obtained than those of the resin compositions obtained by using each antimicrobial agent alone.

As described above, the antimicrobial resin composition of the present invention has excellent dispersibility, discoloration resistance and antimicrobial properties by using the specific two kinds of antimicrobial agents together, and is useful for rendering products antimicrobial, such as stationery, daily necessities, home electric appliances, building materials, and textile products.

What is claimed is:

1. An antimicrobial resin composition, wherein the composition comprises:
   100 parts by weight of a resin (A),
   0.01 to 10 parts by weight of an antimicrobial agent (B) which is a zeolite carrying at least one metal ion selected from the group consisting of silver, copper, zinc and tin, and
   0.01 to 10 parts by weight of an antimicrobial agent (D) which is a soluble glass powder containing silver ion, and
   wherein the average particle diameter of the antimicrobial agent (B) is 0.2 to 10 µm and the average particle diameter of the antimicrobial agent (D) is 0.3 to 10 µm.

2. The antimicrobial resin composition according to claim 1, wherein the resin (A) is polystyrene, polyamide, polyester, polyvinyl alcohol, polycarbonate, polyacetal, ABS resin, acrylic resin, fluorocarbon resin, polyurethane elastomer, or polyester elastomer.

3. The antimicrobial resin composition according to claim 2, wherein the resin (A) is polystyrene, polycarbonate, or ABS resin.

4. The antimicrobial resin composition according to claim 1, wherein the antimicrobial agent (B) is a zeolite carrying zinc ion.

5. The antimicrobial resin composition according to claim 1, wherein the average particle diameter of the antimicrobial agent (B) is 2 to 5 µm.

6. The antimicrobial resin composition according to claim 1, wherein the average particle diameter of the antimicrobial agent (D) is 0.5 to 2 µm.

7. An antimicrobial resin composition which exhibits discoloration resistance,
   wherein the composition is a blend of a resin (A), an antimicrobial agent (B) and an antimicrobial agent (D),
   wherein the antimicrobial agent (B) is a zeolite carrying at least one metal ion selected from the group consisting of silver, copper, zinc and tin;
   wherein the antimicrobial agent (D) is a soluble glass powder which contains silver ion; and
   wherein the average particle diameter of the antimicrobial agent (B) is 0.2 to 10 µm and the average particle diameter of the antimicrobial agent (D) is 0.3 to 10 µm.

* * * * *